United States Patent

Kawashima

Patent Number: 6,084,133
Date of Patent: Jul. 4, 2000

[54] PROCESSES FOR PRODUCING SECONDARY PHOSPHINES

[75] Inventor: Masatoshi Kawashima, Kanagawa, Japan

[73] Assignee: Kankyo Kagaku Center Co., Ltd., Kanagawa-ken, Japan

[21] Appl. No.: 09/409,280

[22] Filed: Sep. 30, 1999

[30] Foreign Application Priority Data

Oct. 2, 1998 [JP] Japan .................................. 10-281386

[51] Int. Cl.$^7$ ..................................................... C07F 9/02
[52] U.S. Cl. ................................................ 568/8; 568/17
[58] Field of Search ........................................... 568/8, 17

[56] References Cited

U.S. PATENT DOCUMENTS

| | | | |
|---|---|---|---|
| 2,959,621 | 11/1960 | Niebergall et al. .................. | 260/606.5 |
| 3,031,509 | 4/1962 | Marshall et al. ..................... | 260/606.5 |
| 3,352,925 | 11/1967 | Hamilton ............................. | 260/606.5 |
| 3,855,311 | 12/1974 | Staendeke ......................... | 260/606.5 P |
| 4,156,697 | 5/1979 | Hestermann et al. ............ | 260/606.5 P |
| 4,163,760 | 8/1979 | Elsner et al. ....................... | 260/606.5 P |

FOREIGN PATENT DOCUMENTS 2703802 8/1978 Germany.

OTHER PUBLICATIONS

Kuchen et al., "Mono-und Oligophenylphosphine", Angewandte Chemie, 68, 791 (1956).
Goldschmidt et al., "Reduktion von Phosphorverbindungen mit Alkalimetallen", Chemische Berichte, 92, 2088 (1959).
"Demethylation of Methyl Aryl Ethers", Organic Syntheses, Coll. vol. 6, p. 569 (1988).
Horner, et al., "Diarylchlorphosphine aus aryldichlorphosphinen durch Disproportionierung", Chem. Ber., 94, 2122 (1961).
Voskuil et al., "Chlorodiisopropylphosphine", Organic Synthesis, Coll, vol. 5, p. 211 (1973).

*Primary Examiner*—Porfirio Nazario-Gonzalez
*Attorney, Agent, or Firm*—Wenderoth, Lind & Ponack, L.L.P.

[57] ABSTRACT

A process for producing a secondary phosphine of formula (2)

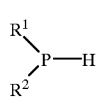

(2)

wherein $R^1$ and $R^2$ may be the same or different and each represent an alkyl group, a cycloalkyl group or an aryl group, each of the above groups being optionally substituted by an alkyl group, an alkoxy group, a halogen atom, a perfluoroalkyl group, an amino group or a phosphino group, which comprises reacting a phosphine halide of formula (1)

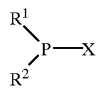

(1)

wherein $R^1$ and $R^2$ are as defined above and X represents a halogen atom, with a metal selected from the metals of Groups 2 to 15 in the Periodic Table or an alloy thereof and reacting the resultant metal di-substituted phosphide with an agent for protonation.

8 Claims, No Drawings

PROCESSES FOR PRODUCING SECONDARY PHOSPHINES

FIELD OF THE INVENTION

This invention relates to a process for producing a secondary phosphine which is useful as a raw material for a phosphine ligand used in the coupling, oxidation and reduction reactions using a transition metal catalyst.

DESCRIPTION OF THE PRIOR ART

Diphenylphosphine has been produced by reducing chlorodiphenylphosphine with lithium aluminum hydride (Angewandte Chemie, 68, 791 (1956)) or by reacting alkali metal diphenylphosphides with water, said diphenylphosphides being prepared from chlorodiphenylphosphine or triphenylphosphine with alkali metal (Chemische Berichte, 92, 2088 (1959), Organic Syntheses, Coll. Vol. 6, p. 569 (1988)).

Further, dicyclohexylphosphine has been produced by an addition reaction of phosphine gas to cyclohexene (DE 2703802), in addition to similar method as mentioned above for diphenylphosphine. Thus the use of such a dangerous water-prohibiting substance as lithium aluminum hydride, metallic sodium, metallic lithium or a highly poisonous phosphine gas resulted in the difficulty in the production of secondary phosphines in an industrial scale or in high yield.

DETAILED DESCRIPTION OF THE INVENTION

As a result of extensive investigation in an effort to solve the above-mentioned problems, we have found that reacting a phosphine halide with one of the metals of Groups 2 to 15 in the Periodic Table or an alloy thereof can produce secondary phosphines safely, simply and easily.

Thus a primary object of the present invention is to provide a practical and simple process for the production of secondary phosphines without use of alkali metals and metal hydrides which are dangerous water-prohibiting substances.

The present invention provides a process for producing a secondary phosphine of formula (2)

(2)

wherein $R^1$ and $R^2$ may be the same or different and each represent an aryl group, an alkyl group or a cycloalkyl group, each of the above groups being optionally substituted by an alkyl group, an alkoxy group, a halogen atom, a perfluoroalkyl group, an amino group or a phosphino group, which comprises reacting a phosphine halide of formula (1)

(1)

wherein $R^1$ and $R^2$ are as defined above and X represents a halogen atom, with a metal selected from the metals of Groups 2 to 15 in the periodic table or an alloy thereof and reacting the resultant metal di-substituted phosphide with an agent for protonation.

The processes of the present invention have the following advantages:

1. It is economical and environment-friendly, because the reaction conditions are relatively mild.
2. It is safe in a water-addition treatment upon completion of the reaction, because substantially all the metals used in the present invention are not a water-prohibiting substance and do not react with water.
3. A solvent can be selected over a broader range, because metals used in the present invention have low reactivity with the solvent.

Accordingly, the process of the present invention can achieve easy scale-up of the production, which results in economical manufacture of secondary phosphines.

The metal used in the present process is selected from the metals of Groups 2–15 in the Periodic Table, which can include metals of Group 2, e.g. Be, Mg; metals of Group 3, e.g. Sc, Y, La, Ce; metals of Group 4, e.g. Ti, Zr, Hf; metals of Group 5, e.g. V, Nb, Ta; metals of Group 6, e.g. Cr, Mo, W; metals of Group 7, e.g. Mn, Re; metals of Group 8, e.g. Fe, Ru, Os; metals of Group 9, e.g. Co, Rh, Ir; metals of Group 10, e.g. Ni, Pd, Pt; metals of Group 11, e.g. Cu, Ag, Au; metals of Group 12, e.g. Zn, Cd, Hg; metals of Group 13, e.g. B, Al, Ga, In, Tl; metals of Group 14, e.g. Si, Ge, Sn, Pb and metals of Group 15, e.g. Sb, Bi. Preferable are Be, Mg, Al, Zn, Ga, Ge, Cd, In, Sn, Sb, Hg, Tl, Pb, Bi,Sc, Ti, V, Cr, Mn, Fe, Co, Ni, Cu, Y, Zr, Nb, Mo, Ru, Rh, Pd, Ag, La, Hf, Ta, W, Re, Os, Ir and Pt. More preferable are metals of Groups 2, 7 and 12–14 in the Periodic Table such as Mg, Mn, Zn, Al and Sn.

The alloy of said metals used in the present process is selected from the alloy consisting of two or more metals of Groups 2–15 in the Periodic Table, examples of which are Wood's alloy (Bi—Pb—Cd—Sn), Rose's alloy (Bi—Sn—Pb), Devarda's alloy (Cu—Al—Zn), Mg—Cu alloy, Mg—Ni alloy, La—Ni—Al alloy, Ca—Ni alloy, Ti—Fe—Mn alloy, Ti—Fe alloy, Pt—Rh alloy, Zr—Ni alloy, Pt—Pd—Au alloy, Ti—Cu alloy, Ni—Al alloy, Ni—Fe alloy, Cu—Mg alloy and Zn—Cu alloy.

The shape of the metals used in the present invention can include, but is not limited to, preferably powders, foils, turnings and granulates, more preferably powders, foils and turnings. The amount of the phosphine halides used for the metals is preferably 0.1 to 10 moles, more preferably 0.5 to 3 moles per mole of the metal, depending on type of the metals used.

The metal may be activated with a small amount of a halogen such as iodine or a halogen-containing compound such as methyl iodide, methyl bromide, 1,2-dibromoethane and chlorotrimethylsilane. Alternatively, an activated metal may be used which is prepared by reducing the corresponding metal halides with an alkaline metal such as lithium and potassium or lithium naphthalenide and the like.

The reaction in the present invention is preferably carried out in the presence of a reaction solvent. The reaction solvents which may be used in the present invention can include an aprotic solvent, preferred examples of which are N,N-dialkyl alkane amides such as N,N-dimethylformamide, N,N-diethylformamide, N,N-dimethylacetamide; N-alkyl lactams such as N-methyl-2-pyrrolidone; 1,3-dialkyl-2-imidazolidinone such as 1,3-dimethyl-2-imidazolidinone; N,N,N',N'-tetraalkylurea such as N,N,N',N'-tetraethylurea; sulfoxides such as dimethyl sulfoxide; nitriles such as acetonitrile; ethers such as diethyl ether, diisopropyl ether, dibutyl ether, 1,4-dioxane, 1,2-dimethoxyethane, tetrahydrofuran; aromatic hydrocarbons such as benzene, toluene, xylene; aliphatic hydrocarbons such as pentane, hexane, heptane; and the mixtures thereof. More preferred solvents can include N,N-dimethylformamide, N,N-diethylformamide, N,N-dimethylacetamide, N-methyl-2-pyrrolidone, 1,3-dimethyl-2-imidazolidinone and tetrahydrofuran.

For the phosphine halides of formula (1) used in the present invention, the alkyl group for $R^1$ and $R^2$ has preferably 1 to 12 carbons, more preferably 1 to 6 carbons, examples of which are methyl, ethyl, propyl, iso-propyl, butyl, t-butyl, hexyl, heptyl, octyl, nonyl, decyl, undecyl, dodecyl. The cycloalkyl group for $R^1$ and $R^2$ has preferably 3 to 12 carbons, more preferably 3 to 6 carbons, examples of which are cyclopropyl, cyclobutyl, cyclohexyl, cycloheptyl, cyclooctyl, cyclononyl, cyclodecyl, cyclododecyl. The aryl group for $R^1$ and $R^2$ is preferably phenyl, tolyl, xylyl and naphthyl.

Each of the alkyl, cycloalkyl and aryl groups as mentioned above for $R^1$ and $R^2$ may be optionally substituted by an alkyl group, preferably of 1 to 4 carbons, an alkoxy group, preferably of 1 to 4 carbons, a halogen atom, a perfluoroalkyl group, an amino group or a phosphino group. The alkyl group as the substituent includes e.g. methyl, ethyl, propyl and t-butyl. The alkoxy group includes e.g. methoxy, ethoxy, propoxy and butoxy. The halogen atom includes e.g. fluorine, chlorine, bromine and iodine. The perfluoroalkyl group includes e.g. trifluoromethyl, nonafluorobutyl and perfluorooctyl. The amino group includes e.g. dimethylamino, dietylamino, diphenylamino and dicyclohexylamino. The phosphino group includes e.g. t-butylchlorophosphino, cyclohexylchlorophosphino, phenylchlorophosphino, methylchlorophosphino, di-t-butylphosphino, dicyclohexylphosphino, diphenylphosphino and dimethylphosphino.

The halogen atom for X in formula (1) includes e.g. fluorine, chlorine, bromine and iodine. Chlorine is preferable.

The phosphine halides used in the present invention include preferably chlorodiarylphosphines, chloroarylalkylphosphines, chlorodialkylphosphines, chlorodicycloalkylphosphines, chloroarylcycloalkylphosphines and chloroalkylcycloalkyl phosphines.

Representative examples of those phosphine halides are chlorodiphenylphosphine, chlorodi(3-methylphenyl)-phosphine, chlorodi(4-methylphenyl)phosphine, chlorobis(2,4-dimethylphenyl)phosphine, chlorobis(3,5-dimethylphenyl)-phosphine, chlorobis(2,6-dimethylphenyl)phosphine, chlorobis(2,4,6-trimethylphenyl)phosphine, chlorobis(3,4,5-trimethylphenyl)phosphine, chlorodi(4-t-butylphenyl)-phosphine, chlorobis(3,5-di-t-butylphenyl)phosphine, chlorodi(3-methoxyphenyl)phosphine, chlorodi(4-methoxyphenyl)phosphine, chlorobis(2,4-dimethoxyphenyl)-phosphine, chlorobis(3,5-dimethoxyphenyl)phosphine, chlorobis(2,6-dimethoxyphenyl)phosphine, chlorobis(2,4,6-trimethoxyphenyl)phosphine, chlorobis(3,4,5-trimethoxyphenyl)phosphine, chlorobis(3,5-dimethyl-4-methoxyphenyl)phosphine, chlorodi(3-chlorophenyl)phosphine, chlorodi(4-chlorophenyl)phosphine, chlorobis(2,4-dichlorophenyl)phosphine, chlorobis(3,5-dichlorophenyl)phosphine, chlorobis(2,6-dichlorophenyl) phosphine, chlorobis(2,4,6-trichlorophenyl)phosphine, chlorobis(3,4,5-trichlorophenyl)phosphine, chlorodi(3-fluorophenyl)phosphine, chlorodi(4-fluorophenyl) phosphine, chlorobis(2,4-difluorophenyl)phosphine, chlorobis(3,5-difluorophenyl)phosphine, chlorobis(2,6-difluorophenyl)phosphine, chlorobis(2,4,6-trifluorophenyl) phosphine, chlorobis(3,4,5-trifluorophenyl)phosphine, chlorobis(3-trifluoromethylphenyl)phosphine, chlorobis(4-trifluoromethylphenyl)phosphine, chlorobis[2,4-bis(trifluoromethyl)phenyl]phosphine, chlorobis[3,5-bis(trifluoromethyl)phenyl]phosphine, chlorobis[2,6-bis(trifluoromethyl)phenyl]phosphine, chlorobis[2,4,6-tris(trifluoromethyl)phenyl]phosphine, chlorobis[3,4,5-tris(trifluoromethyl)phenyl]phosphine, chlorobis(3-dimethylaminophenyl]phosphine, chlorobis(4-dimethylaminophenyl]phosphine, chlorobis[2,4-bis(dimethylamino)phenyl]phosphine, chlorobis[3,5-bis(dimethylamino)phenyl]phosphine, chlorobis[2,6-bis(dimethylamino)phenyl]phosphine, chlorobis[2,4,6-tris(dimethylamino)phenyl]phosphine, chlorobis[3,4,5-tris(dimethylamino)phenyl]phosphine, chlorobis(3-biphenyl) phosphine, chlorobis(4-biphenyl)phosphine, chlorobis(2,4-diphenylphenyl)phosphine, chlorobis(3,5-diphenylphenyl) phosphine, chlorobis(2,6-diphenylphenyl)phosphine, chlorobis(2,4,6-triphenylphenyl)phosphine, chlorobis(3,4,5-triphenylphenyl)phosphine, chlorodi(α-naphthyl) phosphine, chlorodi(β-naphthyl)phosphine, chlorodi(6-methoxy-α-naphthyl)phosphine, chlorodi(6-methoxy-β-naphthyl)phosphine, chlorodi(3,4-methylenedioxyphenyl) phosphine, chlorodimethylphosphine, chlorodiethylphosphine, chlorodi-tert-butylphosphine, chlorodicyclopropylphosphine, chlorodicyclopentylphosphine, chlorodicyclohexylphosphine, chlorodicyclooctylphosphine, chlorodicyclodecylphosphine, chlorodicyclododecylphosphine, chlorocyclohexylphenylphosphine, 1,3-bis(phenylchlorophosphino)propane and 1,2-bis(phenylchlorophosphino)benzene.

The phosphine halides of formula (1) can be prepared by a method such as a disproportionation of phenylphosphonous dichloride (Chem. Ber., 94, 2122 (1961)) and an alkylation of phosphorus trichloride with Grignard reagent (Organic Synthesis, Coll, Vol. V, p. 211, (1973)).

For the secondary phosphines of formula (2) prepared by the process of the present invention, $R^1$ and $R^2$ have the same meanings as mentioned above for the phosphine halides of formula (1). Further, $R^1$ and $R^2$ may have the substituents, examples of which are as recited above for the formula (1).

The secondary phosphines of formula (2) include preferably diarylphosphines, arylalkylphosphines, dialkylphosphines, dicycloalkylphosphines, arylcycloalkylphosphines and alkylcycloalkylphosphines.

Representative examples of those secondary phosphines are diphenylphosphine, di(3-methylphenyl)phosphine, di(4-methylphenyl)phosphine, bis(2,4-dimethylphenyl) phosphine, bis(3,5-dimethylphenyl)phosphine, bis(2,6-dimethylphenyl)phosphine, bis(2,4,6-trimethylphenyl) phosphine, bis(3,4,5-trimethylphenyl)phosphine, di(4-t-butylphenyl)phosphine, bis(3,5-di-t-butylphenyl)phosphine, di(3-methoxyphenyl)phosphine, di(4-methoxyphenyl) phosphine, bis(2,4-dimethoxyphenyl)phosphine, bis(3,5-dimethoxyphenyl)phosphine, bis(2,6-dimethoxyphenyl) phosphine, bis(2,4,6-trimethoxyphenyl)phosphine, bis(3,4,5-trimethoxyphenyl)phosphine, bis(3,5-dimethyl-4-methoxyphenyl)phosphine, di(3-chlorophenyl)phosphine, di(4-chlorophenyl)phosphine, bis(2,4-dichlorophenyl) phosphine, bis(3,5-dichlorophenyl)phosphine, bis(2,6-dichlorophenyl)phosphine, bis(2,4,6-trichlorophenyl) phosphine, bis(3,4,5-trichlorophenyl)phosphine, di(3-fluorophenyl)phosphine, di(4-fluorophenyl)phosphine, bis(2,4-difluorophenyl)phosphine, bis(3,5-difluorophenyl)

phosphine, bis(2,6-difluorophenyl)phosphine, bis(2,4,6-trifluorophenyl)phosphine, bis(3,4,5-trifluorophenyl)phosphine, di(3-trifluoromethylphenyl)phosphine, di(4-trifluoromethylphenyl)phosphine, bis(2,4-bistrifluoromethylphenyl)phosphine, bis(3,5-bistrifluoromethylphenyl)phosphine, bis(2,6-bistrifluoromethylphenyl)phosphine, bis(2,4,6-tristrifluoromethylphenyl)phosphine, bis(3,4,5-tristrifluoromethylphenyl)phosphine, di(3-dimethylaminophenyl)phosphine, di(4-dimethylaminophenyl)phosphine, bis(2,4-bisdimethylaminophenyl)phosphine, bis(3,5-bisdimethylaminophenyl)phosphine, bis(2,6-bisdimethylaminophenyl)phosphine, bis(2,4,6-trisdimethylaminophenyl)phosphine, bis(3,4,5-trisdimethylaminophenyl)phosphine, di(3-biphenyl)phosphine, di(4-biphenyl)phosphine, bis(2,4-diphenylphenyl)phosphine, bis(3,5-diphenylphenyl)phosphine, bis(2,6-diphenylphenyl)phosphine, bis(2,4,6-triphenylphenyl)phosphine, bis(3,4,5-triphenylphenyl)phosphine, di($\alpha$-naphthyl)phosphine, di($\beta$-naphthyl)phosphine, di(6-methoxy-$\alpha$-naphthyl)phosphine, di(6-methoxy-$\beta$-naphthyl)phosphine, di(3,4-methylenedioxyphenyl)phosphine, dimethylphosphine, diethylphosphine, dicyclopropylphosphine, dicyclopentylphosphine, dicyclohexylphosphine, dicyclooctylphosphine, dicyclodecylphosphine, dicyclododecylphosphine, cyclohexylphenylphosphine, 1,3-bis(phenylphosphino)propane and 1,2-bis(phenylphosphino)benzene.

A reaction temperature between phosphine halides and metals (or alloys thereof) is a temperature between not lower than the melting point of the reaction solvents and not higher than the boiling point of the reaction solvent, preferably from 0° C. to 150° C. and more preferably from 20° C. to 100° C. A reaction time ranges from 30 minutes to 48 hours, depending on kind and shape of the metal, solvent, reaction temperature and agitating speed.

The reaction procedures in the present invention are carried out in any order. The solvents, metals or alloys thereof and phosphine halides may be added in any order.

The agents for protonation to be reacted with the resultant metal di-substituted phosphides after completion of the reaction between the phosphine halides and the metals or alloys thereof can include preferably water; mineral acids such as hydrochloric acid, sulfuric acid, nitric acid, phosphoric acid; carboxylic acids such as acetic acid, propionic acid; phenols such as phenol, cresol; and alcohols such as methanol, ethanol, more preferably water, dilute hydrochloric acid, dilute sulfuric acid. The amount of the agent for protonation added is at least 1.0 equivalent relative to the phosphine halide. Usually, it is preferable that the agent for protonation is used in large excess, for the purpose of separating a water-soluble reaction solvent and a non-water soluble solvent added for extraction of the resulting secondary phosphines.

The metal di-substituted phosphides produced by reaction of the phosphine halides with the metals or the alloys thereof can be represented by the following formula (3)

$$(R^1R^2P)_m M_k X_n \quad (3)$$

in which $R^1$, $R^2$ and X are as defined above, M represents a metal selected from the metals of Groups 2 to 15 in the periodic table or the alloy thereof, having the relationship of v=(m+n)/k, assuming that the valence of metal is v. m and n are different from each other, depending on the metal used.

It is presumed that a mixture of the metal di-substituted phosphides having different m and n is formed even one metal is used.

The process of the present invention is illustrated below. The aprotic solvent is added to the metal in an atmosphere of an inert gas, the phosphine halide is added dropwise with stirring to the mixture and finally dilute hydrochloric acid is added dropwise to cease the reaction. Then a solvent such as toluene is added and the resultant secondary phosphine is extracted. The toluene layer and the aqueous layer are separated off. A toluene solution in which the secondary phosphine is dissolved can be used as such for other reaction, and if necessary, this toluene solution is concentrated under reduced pressure to afford the secondary phosphine which may be purified by distillation.

The invention is further illustrated by the following Examples.

EXAMPLE 1

1.04 g (4.71 mmol) of chlorodiphenylphosphine was added dropwise in a nitrogen gas atmosphere to a suspension of 461 mg (7.05 mg-atoms) of zinc (powder) in 10 cm³ of N,N-dimethylformamide and the mixture was stirred at room temperature for one hour. To the reaction mixture was added dropwise 10 cm³ (10 mmol) of 1 mol·dm⁻³ hydrochloric acid and then 10 cm³ of toluene. The mixture was stirred, the aqueous layer and the toluene layer were separated off, the toluene layer was dried over anhydrous sodium sulfate and concentrated under reduced pressure, giving 551 mg (2.96 mmol) of diphenylphosphine in 63% yield.

EXAMPLES 2–28

A similar procedure as in Example 1 was carried out varying sort and amount of the metal, solvent and on time. The results are shown in Table 1. The yield terminated by gas chromatography.

TABLE 1

| Example | Metal (shape) | Molar ratio* | Solvent | Reaction time (hr.) | yield (%) |
|---|---|---|---|---|---|
| 2 | Zn (powder) | 1.1 | N,N-dimethyl formamide | 1 | 55 |
| 3 | Zn (pdwder) | 3.0 | N,N-dimethyl formamide | 1 | 45 |
| 4 | Zn (powder) | 1.5 | N,N-dimethyl acetamide | 1 | 59 |
| 5 | Zn (powder) | 1.5 | N-methyl-2-pyrrolidone | 1 | 59 |
| 6 | Zn (powder) | 1.5 | 1,3-dimethyl-2-imidazoli-dinone | 1 | 45 |
| 7 | Zn (powder) | 1.5 | tetrahydrofuran | 1 | 62 |
| 8 | Zn (powder) | 1.5 | toluene | 1 | 35 |
| 9 | Zn (powder) | 1.5 | N,N-dimethyl formamide | 20 | 63 |
| 10 | Mg (turnings) | 1.5 | N,N-dimethyl formamide | 1 | 20 |
| 11 | Mg (turnings) | 1.5 | N,N-dimethyl formamide | 20 | 68 |
| 12 | Mg (turnings) | 1.5 | tetrahydrofuran | 20 | 68 |
| 13 | Al (foil) | 1.5 | N,N-dimethyl formamide | 20 | 56 |
| 14 | Al (foil) | 0.67 | N,N-dimethyl formamide | 20 | 49 |
| 15 | Sn (powder) | 1.5 | N,N-dimethyl formamide | 20 | 72 |
| 16 | Sn (powder) | 0.5 | N,N-dimethyl formamide | 20 | 75 |

TABLE 1-continued

| Example | Metal (shape) | Molar ratio* | Solvent | Reaction time (hr.) | yield (%) |
|---|---|---|---|---|---|
| 17 | Ti (powder) | 1.5 | N,N-dimethyl formamide | 20 | 19 |
| 18 | Cr (powder) | 1.5 | N,N-dimethyl formamide | 20 | 23 |
| 19 | Cr (powder) | 0.5 | N,N-dimethyl formamide | 20 | 34 |
| 20 | Mn (powder) | 1.5 | N,N-dimethyl formamide | 20 | 48 |
| 21 | Mn (powder) | 0.67 | N,N-dimethyl formamide | 20 | 67 |
| 22 | Mn (powder) | 0.5 | N,N-dimethyl formamide | 20 | 72 |
| 23 | Fe (powder) | 1.5 | N,N-dimethyl formamide | 20 | 30 |
| 24 | Fe (powder) | 0.67 | N,N-dimethyl formamide | 20 | 36 |
| 25 | Co (powder) | 1.5 | N,N-dimethyl formamide | 20 | 19 |
| 26 | Ni (powder) | 1.5 | N,N-dimethyl formamide | 20 | 8 |
| 27 | Cu (powder) | 1.5 | N,N-dimethyl formamide | 20 | 16 |
| 28 | Devarda's alloy (powder) | 1.5 | N,N-dimethyl formamide | 20 | 58 |

Note: Molar ratio* shows a molar ratio of metal/chlorodiphenylphosphine.

EXAMPLE 29

$20 \times 10^{-3}$ cm$^3$ of 1,2-dibromoethane was added dropwise in a nitrogen gas atmosphere to a suspension of 461 mg (7.05 mg-atoms) of zinc (powder) in 10 cm$^3$ of tetrahydrofuran, the mixture was heated to reflux for about 2 minutes and cooled to room temperature, $30 \times 10^{-3}$ cm$^3$ of chlorotrimethylsilane was added and the mixture was stirred for about 2 minutes to prepare an activated zinc. Subsequently, 1.04 g (4.71 mmol) of chlorodiphenylphosphine was added dropwise and the mixture was stirred at room temperature. To the reaction mixture was added dropwise 10 cm$^3$ (10 mmol) of 1 mol·dm$^{-3}$ hydrochloric acid and then 10 cm$^3$ of toluene. The mixture was stirred, the aqueous layer and the toluene layer were separated off, the toluene layer was determined by gas chromatography, giving diphenylphosphine in 84% yield.

EXAMPLE 30

1.09 g (4.68 mmol) of chlorodicyclohexylphosphine was added dropwise in a nitrogen gas atmosphere to a suspension of 461 mg (7.05 mg-atoms) of zinc (powder) in 10 cm$^3$ of N,N-dimethylformamide and the mixture was stirred at room temperature for one hour. To the reaction mixture was added dropwise 10 cm$^3$ (10 mmol) of 1 mol·dm·$^{-3}$ hydrochloric acid and then 10 cm$^3$ of toluene. The mixture was stirred, the aqueous layer and the toluene layer were separated off, and the toluene layer was determined by gas chromatography, giving dicyclohexylphosphine in 67% yield.

EXAMPLE 31

0.849 g (4.70 mmol) of chloro-di-t-butylphosphine was added dropwise in a nitrogen gas atmosphere to a suspension of 461 mg (7.05 mg-atoms) of zinc (powder) in 10 cm$^3$ of N,N-dimethylformamide and the mixture was stirred at room temperature for one hour. To the reaction mixture was added dropwise 10 cm$^3$ (10 mmol) of 1 mol·dm$^{-3}$ hydrochloric acid and then 10 cm$^3$ of toluene. The mixture was stirred, the aqueous layer and the toluene layer were separated off, and the toluene layer was determined by gas chromatography, giving di-t-butylphosphine in 25% yield.

EXAMPLE 32

The reduction of chloro-di-t-butylphosphine was conducted in a similar manner as in Example 31, but the activated zinc was prepared as in Example 29, giving di-t-butylphosphine in 31% yield.

EXAMPLE 33

1.04 g (4.71 mmol) of chlorodiphenylphosphine was added dropwise under a nitrogen gas atmosphere to a suspension of 127 mg (4.71 mmol) of aluminum (foil) in 10 cm$^3$ of N,N-dimethylformamide and the mixture was stirred at 100° C. for 30 min. To the reaction mixture was added dropwise 10 cm$^3$ (10 mmol) of 1 mol·dm$^{-3}$ hydrochloric acid and then 10 cm$^3$ of toluene. The mixture was stirred, the aqueous layer and the toluene layer were separated off, the toluene layer was dried over anhydrous sodium sulfate and concentrated under reduced pressure, giving 763 mg (4.10 mmol) of diphenylphosphine in 87% yield.

EXAMPLE 34

1.04 g (4.71 mmol) of chlorodiphenylphosphine was added dropwise under a nitrogen gas atmosphere to a suspension of 254 mg (9.42 mmol) of aluminum (foil) in 10 cm$^3$ of N,N-dimethylformamide and the mixture was stirred at 100° C. for 30 min. To the reaction mixture was added dropwise 10 cm$^3$ (10 mmol) of 1 mol·dm$^{-3}$ sulfuric acid and then 10 cm$^3$ of toluene. The mixture was stirred, the aqueous layer and the toluene layer were separated off, the toluene layer was dried over anhydrous sodium sulfate and concentrated under reduced pressure, giving 737 mg (3.96 mmol) of diphenylphosphine in 84% yield.

EXAMPLE 35

1.04 g (4.71 mmol) of chlorodiphenylphosphine was added dropwise under a nitrogen gas atmosphere to a suspension of 229 mg (9.42 mmol) of magnesium (turning) in 10 cm$^3$ of N,N-dimethylformamide and the mixture was stirred at 100° C. for one hour. To the reaction mixture was added dropwise 10 cm$^3$ (10 mmol) of 1 mol·dm$^{-3}$ phosphoric acid and then 10 cm$^3$ of toluene. The mixture was stirred, the aqueous layer and the toluene layer were separated off, the toluene layer was dried over anhydrous sodium sulfate and concentrated under reduced pressure, giving 710 mg (3.81 mmol) of diphenylphosphine in 81% yield.

EXAMPLE 36

1.04 g (4.71 mmol) of chlorodiphenylphosphine was added dropwise under a nitrogen gas atmosphere to a suspension of 129 mg (2.35 mmol) of manganese (powder) in 10 cm3 of N,N-dimethylformamide and the mixture was stirred at 100° C. for 6 hours. To the reaction mixture was added dropwise 601 mg (10 mmol) of acetic acid and then 10 cm$^3$ of water and 10 cm$^3$ of toluene. The mixture was stirred, the aqueous layer and the toluene layer were separated off, the toluene layer was dried over anhydrous sodium sulfate and concentrated under reduced pressure to give 675 mg (3.63 mmol) of diphenylphosphine in 77% yield.

EXAMPLE 37

1.04 g (4.71 mmol) of chlorodiphenylphosphine was added dropwise under a nitrogen gas atmosphere to a suspension of 461 mg (7.05 mmol) of zinc (powder) in 10 cm³ of tetrahydrofuran and the mixture was stirred at 50° C. for one hour. To the reaction mixture was added dropwise 170 mg (9.43 mmol) of water. The mixture was stirred, and the organic layer was filtered. The filtrate was concentrated under reduced pressure to give 526 mg (2.82 mmol) of diphenylphosphine in 60% yield.

EXAMPLE 38

1.50 g (9.46 mmol) of chloromethylphenylphosphine was added dropwise under a nitrogen gas atmosphere to a suspension of 922 mg (14.1 mmol) of zinc (powder) in 20 cm³ of N,N-dimethylformamide and the mixture was stirred at 100° C. for 30 min. To the reaction mixture was added dropwise 10 cm³ (10 mmol) of 1 mol·dm⁻³ hydrochloric acid and then 20 cm³ of toluene. The mixture was stirred, the aqueous layer and the toluene layer were separated off, the toluene layer was dried over anhydrous sodium sulfate and concentrated under reduced pressure, giving 975 mg (7.85 mmol) of methylphenylphosphine in 83% yield.

INDUSTRIAL APPLICABILITY

According to the present invention, the secondary phosphines can be produced safely, simply and easily in high yield by reacting the phosphine halides with the metals or alloys thereof, followed by reaction with the agent for protonation.

What is claimed is:

1. A process for producing a secondary phosphine of formula (2)

(2)

wherein R¹ and R² may be the same or different and each represent an alkyl group, a cycloalkyl group or an aryl group, each of the above groups being optionally substituted by an alkyl group, an alkoxy group, a halogen atom, a perfluoroalkyl group, an amino group or a phosphino group, which comprises reacting a phosphine halide of formula (1)

(1)

wherein R¹ and R² are as defined above and X represents a halogen atom, with a metal selected from the metals of Groups 2 to 15 in the Periodic Table or an alloy thereof and reacting the resultant metal di-substituted phosphide with an agent for protonation.

2. The process of claim 1 wherein the reaction is carried out in the presence of a reaction solvent.

3. The process of claim 1 wherein the metal is selected from the metals of Groups 2, 7 and 12–14 in the Periodic Table.

4. The process of claim 1 wherein the metal is Zn, Mg, Al, Sn or Mn.

5. The process of claim 1 wherein the agent for protonation is selected from water, mineral acids, carboxylic acids, phenols and alcohols.

6. The process of claim 1 wherein the agent for protonation is water, hydrochloric acid or sulfuric acid.

7. The process of claim 1 wherein the resultant metal di-substituted phosphide is represented by the following formula (3)

$$(R^1R^2P)_m M_k X_n \qquad (3)$$

in which R¹, R² and X are as defined above, M represents a metal selected from the metals of Groups 2 to 15 in the Periodic Table or the alloy thereof, having the relationship of v=(m+n)/k, assuming that the valence of metal is v, and m and n are different from each other, depending on the metal used.

8. The process of claim 1 wherein the phosphine halide is the compound of formula (1) in which R¹ and R² each represent an alkyl group of 1 to 12 carbons, a cycloalkyl group of 3 to 12 carbons or an aryl group and X is chlorine.

* * * * *